US011647906B2

(12) United States Patent
    Kasprzak

(10) Patent No.: US 11,647,906 B2
(45) Date of Patent: May 16, 2023

(54) DERMOSCOPE AND METHODS

(71) Applicant: Michal Pawel Kasprzak, Falenty Duze (PL)

(72) Inventor: Michal Pawel Kasprzak, Falenty Duze (PL)

(*) Notice: Subject to any disclaimer, the term of this patent is extended or adjusted under 35 U.S.C. 154(b) by 374 days.

(21) Appl. No.: 16/636,119

(22) PCT Filed: Jul. 16, 2018

(86) PCT No.: PCT/EP2018/069262
    § 371 (c)(1),
    (2) Date: Feb. 3, 2020

(87) PCT Pub. No.: WO2019/025175
    PCT Pub. Date: Feb. 7, 2019

(65) Prior Publication Data
    US 2021/0161390 A1    Jun. 3, 2021

(30) Foreign Application Priority Data
    Aug. 3, 2017  (PL) .......................................... 422438

(51) Int. Cl.
    *A61B 5/00*    (2006.01)
(52) U.S. Cl.
    CPC ............ *A61B 5/0077* (2013.01); *A61B 5/441* (2013.01); *A61B 5/448* (2013.01)
(58) Field of Classification Search
    CPC .......................... A61B 5/0059; G01N 21/4738
    USPC ....................................................... 600/306
    See application file for complete search history.

(56) References Cited

U.S. PATENT DOCUMENTS

| | | | |
|---|---|---|---|
| 2002/0118370 A1* | 8/2002 | Nishida | G01M 11/0271 356/515 |
| 2003/0045799 A1 | 3/2003 | Bazin et al. | |
| 2004/0062056 A1 | 4/2004 | Heine et al. | |
| 2007/0058260 A1* | 3/2007 | Steenblik | G02B 30/27 359/626 |
| 2010/0208050 A1* | 8/2010 | Wadman | A61B 5/442 348/E7.085 |

(Continued)

FOREIGN PATENT DOCUMENTS

EP    2040061 A1    3/2009

OTHER PUBLICATIONS

International Search Report and Written Opinion for PCT Patent App. No. PCT/EP2018/069262 (dated Nov. 8, 2018).

*Primary Examiner* — Fabricio R Murillo Garcia
(74) *Attorney, Agent, or Firm* — Whitestone Law, PLLC

(57) ABSTRACT

Some embodiments are directed to a dermoscope and a method for forming an image of a part of a skin having one or more at least partly transparent structures, such as at least partly transparent hair. The dermoscope has a light source, a light shaping unit, and an image forming lens. The light source is arranged to provide light to the light shaping unit. The light shaping unit is arranged to direct at least part of the light via an immersion fluid to the part of the skin having the one or more at least partly transparent structures to be imaged at incident angles in the immersion fluid larger than 70 degrees relative to the optical axis of the dermoscope. The image forming lens is arranged to receive at least light refracted from the one or more at least partly transparent structures.

15 Claims, 8 Drawing Sheets

(56) References Cited

U.S. PATENT DOCUMENTS

| | | | | |
|---|---|---|---|---|
| 2015/0036311 A1* | 2/2015 | Mullani | ............... | A61B 5/0059 |
| | | | | 362/230 |
| 2015/0051593 A1* | 2/2015 | Johnson | ............... | A61N 5/0616 |
| | | | | 606/17 |
| 2017/0286752 A1* | 10/2017 | Gusarov | .............. | G06V 40/165 |

* cited by examiner

DERMOSCOPE AND METHODS

CROSS REFERENCE TO RELATED APPLICATIONS

This application is a national phase filing under 35 C.F.R. § 371 of and claims priority to PCT Patent Application No. PCT/EP2018/069262, filed on Jul. 16, 2018, which claims the priority benefit under 35 U.S.C. § 119 of Polish Patent Application No. P.422438, filed on Aug. 3, 2017, the contents of each of which are hereby incorporated in their entireties by reference.

BACKGROUND

The presently disclosed subject matter relates to a dermoscope, a sub-assembly for a dermoscope, associated methods, and a computer program product.

Hair condition, in particular hair disorders, have traditionally been assessed by clinical inspection and a number of invasive methods including a pull-test, a trichogram obtained from extraction of approximately hundred hairs for microscopic inspection of their roots, and patomorphology which uses biopsy after extraction of skin tissue for microscopic inspection.

In 2006, it was proposed by Ross, E K, Vincenzi, C I, and Tosti, A. that a dermoscope or videodermoscope, traditionally used for skin lesion observations, may be used for diagnosing hair disorders. Since then their method, usually referred to as trichoscopy, has gained some popularity due to its non-invasiveness. A number of studies have been carried out to provide guidelines for disease diagnosis based on visual, qualitative inspection of the videodermosopy images by a trained dermatologist doctor. Visual trichoscopy has generally focused on setting the initial diagnosis based on certain characteristic features observed in the dermoscopy images of the scalp, such as broken hair, yellow dots, black dots, tulip hair, arborizing vessels, etc.

The term dermoscopy may further be used to refer to a technique used in the assessment of skin condition, examination of symptoms of skin disorder, diagnosis of skin disorders, and monitoring skin treatment efficiency. The term trichoscopy may further be used to refer to a technique used in the assessment of hair condition, examination of symptoms of hair disorder, diagnosis of hair disorders, and monitoring hair treatment efficiency. Dermoscopy and trichoscopy generally uses a microscopic camera, a so-called dermoscope or videodermoscope to register high resolution images of hair and scalp or other skin. Such images may further be referred to as dermoscopy images or videodermoscopy images. The dermoscope may have an image sensor, allowing to capture the dermoscopy images. The dermoscope may be a so-called manual dermoscope where the image is directly observed through an eyepiece with the user's eye. Dermoscopy and trichoscopy image registration is usually performed with the use of immersion fluid or polarized light to reduce skin surface reflections. Herein, water or alcohol is usually used as immersion fluid. In known trichoscopy methods, the videodermoscopy images are subject to manual or computer-assisted analysis to try to identify all or most hair shafts and measure hair diameters. A statistical analysis of images registered before and after the treatment allows to assess the response to treatment in terms of, for example, hair number or hair density, hair thickness, hair length, hair volume, hair colour, hair regrowth, or, in case of epilation, hair extraction, as well as—simultaneously or alternatively—the effect of treatment on the skin. Known dermoscopes and methods suffer from various limitations. For example, it may be difficult or even impossible to register images of grey, blond or white hair at all and/or with sufficient quality to perform accurate and/or reliable measurements on these grey, blond or white hair. Common practice in measurements of gray, blond or white hair is dying the hair and performing the measurements on dyed hair; such dying is considered inconvenient and also prevents measurements of the natural condition of the hair. Also dermoscopy suffers from some limitations; for example, it may be difficult to register images of structures in the epidermis which show little contrast with their environment. Thus, there is a wish to alleviate one or more of the above mentioned limitations.

SUMMARY

A first aspect of the presently disclosed subject matter provides a dermoscope for forming an image of a part of a skin having one or more at least partly transparent structures, such as at least party transparent hair. The dermoscope includes a light source, a light shaping unit and an image forming lens. The light source, the light shaping unit and the image forming lens being arranged and aligned on an optical axis of the dermoscope. The light source is arranged to provide light to the light shaping unit. The light shaping unit is arranged to direct at least part of the light via an immersion fluid to the part of the skin having the one or more at least partly transparent structures to be imaged at incident angles in the immersion fluid larger than 70 degrees relative to the optical axis of the dermoscope. The image forming lens is arranged to receive at least part of the light refracted by the one or more at least partly transparent structures. The image forming lens may be arranged to receive light refracted by the one or more at least partly transparent structures at angles within a field-of-view angular range of the image forming lens. The field-of-view angular range may, for example, be an opening angle between 1 and 40 degrees in air centered about the optical axis of the image forming lens, such as between 2 and 20 degrees, such as about 10-12 degrees, or narrower angular ranges in a narrow-angle dermoscope, such as between 2 and 10 degrees, such as about 5 degrees. The dermoscope may include a sensor and the image forming lens may be arranged to image onto a sensor, the sensor being further arranged to register the image from at least the detected light. The dermoscope may include an eyepiece and the image forming lens may be part of the eyepiece or arranged to cooperate with the eyepiece. The one or more at least partly transparent structures may include at least party transparent hair, such as grey, blond or transparent hair. The one or more at least partly transparent structures may additionally or alternatively include other structures of a similar refractive index as at least partly transparent hair. The one or more at least partly transparent structures may additionally or alternatively include structures on the surface of the skin, or in an upper layer of the skin, such as hair follicles, in particular empty hair follicles. During use, the direction of the optical axis of the dermoscope may correspond, at least substantially, with the direction of the normal of the skin surface. Thus, the term "normal of the skin surface" may be used in the following to refer to "The optical axis of the dermoscope" or "the direction of the optical axis of the dermoscope". The optical axis of the dermoscope may correspond to the optical axis of the image forming lens. The optical axis of the dermoscope may correspond to the optical axis of the light forming unit. In the following, the terms "the light refracted from the part of the skin" and "the light refracted from the part of the skin having the one or more at least partly transparent structures" may be used to refer to "the light refracted from the one or more at least partly transparent structures", and the term "the part of the skin" may be used to refer to "the part of the skin having the one or more at least partly transparent structures" in a concise manner. The dermoscope according to the first aspect allows for detecting and imaging transparent, grey or blond hair using refraction and total internal reflection at the hairs inner surface, rather than reflection at it outer surface. Hereto, light is provided at high angles, such as 70-80° in the immersion fluid relative to the normal to the skin surface. This high-angle light is refracted into the hair, reflected by total internal reflection at the inner surface of the hair, and refracted out of the hair towards the camera lens and sensor—or the eyepiece—, at lower angles, for example below 20° relative to the normal to the skin surface. The image forming lens may hereto be arranged to receive at least part of the light refracted by the one or more at least partly transparent structures to the image forming lens at angles in the immersion fluid smaller than 20 degrees relative to the normal. Transparent, grey, and blond hair may thus be imaged, whereas standard dermoscopes using white light and reflection can image pigmented, opaque objects like dark hair but not gray, blond and white. In the following, the term "receive at least part of the light refracted from the part of the skin" may be used to refer to "receive at least part of the light refracted from the one or more at least partly transparent structures" in a concise manner. In the following, the term "image of the part of the skin" may be used to refer, in a concise manner, to "image of the part of the skin and structures of the skin" or to "image of the part of the skin and transparent, refractive and/or reflective structures of the skin". In the following, reference will be made to trichoscopy with high-angle illumination and detection of the high-angle light refracted by transparent hair as refractive trichoscopy; known trichoscopy with reflective imaging may be referred to as reflective trischoscopy. In the following, the term "transparent hair" may be used to refer to "transparent, grey or blond hair", or to any one transparent, grey and blond hair. Hair is known to have a refractive index in a range of n(hair)=1.545-1.550. The light shaping unit may be a solid glass body, a solid plastic body, or a solid body of another suitable material having a refractive index in a range of n(HIN)=1.45-1.60, such as in a range of n(HIN)=1.49-1.52. The light shaping unit may, for example, be made of PMMA and have a refractive index of n(HIN)= 1.49 for an exemplary PMMA material. The light shaping unit may alternatively, for example, be made of a glass material having a refractive index of n(HIN)=1.50-1.52 for exemplary glass materials. The light shaping unit may alternative, for example, made of a polycarbonate material having a refractive index of (HIN)=1.60 for an exemplary polycarbonate material. The light shaping unit may be an integrally formed body. The light shaping unit may be composed of a plurality of separately manufactured optical parts which are glued or otherwise connected together to form a substantially solid body. The immersion fluid may be any suitable immersion fluid such as water or alcohol. The immersion fluid may in particular be water which has a refractive index of about n(water)≈1.34, slightly lower than the refractive index of alcohol n(alcohol)≈1.37, whereby water has a critical angle of a water-air interface of about 49 degrees in water and alcohol has a critical angle of an alcohol-air interface of about 47 degrees in alcohol; thus, the use of water as immersion fluid may allow an easier detection of the refracted light. In an embodiment, water is used as the immersion fluid, the light shaping unit is a solid optical component with a refractive index in a range of 1.49-1.52, and the light shaping unit is arranged to direct at least part of the light via the immersion fluid to the part of the skin having the one or more at least partly transparent structures to be imaged at incident angles in the immersion fluid larger than 70 degrees, such as in a range of 72-76 degrees, relative to the optical axis of the dermoscope. In another embodiment, alcohol is used as the immersion fluid, the light shaping unit is a solid optical component with a refractive index in a range of 1.49-1.52, and the light shaping unit is arranged to direct at least part of the light via the immersion fluid to the part of the skin having the one or more at least partly transparent structures to be imaged at incident angles in the immersion fluid larger than 77 degrees, such as in a range of 79-83 degrees, relative to the optical axis of the dermoscope.

Embodiments according to the first aspect may thus provide a dermoscope for forming an image of a part of a skin having one or more at least partly transparent structures immersed in an immersion fluid, the dermoscope including a light source, a light shaping unit and an image forming lens, the light source being arranged to provide light to the light shaping unit, the light shaping unit having an externally exposed contact surface for being in contact with the immersion fluid, the light source and the light shaping unit being arranged to provide at least part of the light provided by the light source to the light shaping unit to the externally exposed contact surface at angles incident on the contact surface larger than 55 degrees inside the light shaping unit relative to the optical axis of the light shaping unit, and the image forming lens being arranged to receive at least part of the light returned through the externally exposed contact surface and the light shaping towards the image forming lens. When the dermoscope is being used for forming an image of a part of a skin having one or more at least partly transparent structures immersed in an immersion fluid, and the externally exposed contact surface is contact with the immersion fluid forming an interface between the light shaping unit and the immersion fluid, the light shaping unit may hereby direct at least part of the light provided by the light source to the light shaping unit via the immersion fluid to the part of the skin having the one or more at least partly transparent structures to be imaged at incident angles in the immersion fluid larger than 70 degrees relative to the optical axis of the dermoscope due to refraction of the light at the interface between the light shaping unit and the immersion fluid provided by the externally exposed contact surface: at least part of the light incident on the contact surface larger than 55 degrees inside the light shaping unit relative to the optical axis of the light shaping unit may be refracted into the immersion fluid at angles larger than 70 degrees relative to the optical axis of the light shaping unit which may at least substantially correspond to the optical axis of the dermoscope. During use, the image forming lens may thus to receive at least part of the light returned by the one or more at least partly transparent structures through the externally exposed contact surface and the light shaping towards the image forming lens. The at least part of the light returned by the one or more at least partly transparent structures through the externally exposed contact surface and the light shaping unit may include of at least part of the light refracted by the one or more at least partly transparent structures.

The various embodiments described below may be used autonomously or in combination of one or more embodiments. The embodiments described may overcome, reduce or alleviate various limitations of known dermoscopy and trichoscopy techniques. The specific limitation or limitations that are overcome, reduced or alleviated by a specific embodiment may be different for the different embodiments and any combinations thereof.

In an embodiment, the dermoscope further includes a further light source. The further light source is arranged to provide further light to the light shaping unit for directing at least part of the further light via the immersion fluid to the part of the skin to be imaged at incident angles in the immersion fluid smaller than 48 degrees relative to the optical axis of the dermoscope. Hereby, the dermoscope does not only use high-angle light for refractive imaging of transparent, grey and blond hair, but also low-angle light for reflective imaging of, in particular, dark hair. The low-angle light may also be used for reflective imaging of the skin surface and reflective structures thereon. The further light source may provide low angle light, which may extend upto the critical angle limited by total internal reflection of 48 degrees in water; projected at around 20 degrees in a possible glass exit window or cover glass of the dermoscope. The low-angle light may substantially correspond to the light used in a related art dermoscope: white light projected at about maximally 20 degrees in the cover glass and maximally 48 degrees in water as immersion fluid, the critical angle as imposed by the a total-internal-reflection to 90 degrees. The high-angle light of the dermoscope according to embodiment of the first aspect may be projected at about 55-65 degrees in the light shaping body and the cover glass and maximally about 70-80 degrees in water as immersion fluid.

In a further embodiment, the dermoscope is arranged to selectively operate the light source and the further light source. Hereby, the high-angle light and the low-angle light may selectively illuminate the part of the skin to selectively obtain a refractive and reflective image. As the refractive image may have a different brightness than the reflective image, obtaining them successively rather than simultaneously may provide a better registration of both types of images and the structures imaged by the two images. The refractive image and reflective image may be combined with appropriate brightness factors to form a combined refractive-reflective image. The dermoscope may for example be arranged to switch between operating the light source and operating the further light source.

In an embodiment, the light source includes one or more LEDs, and the one or more LEDs are in direct optical contact to the light shaping unit. The one or more LEDs are hereby arranged to couple light into the light shaping unit at angles larger than 55 degrees relative to the optical axis of the light shaping unit. The LEDs may thus be attached to the light shaping unit and be arranged to provide light to the part of the skin without any n=1 material or air layer in between, i.e., without being prevented by the critical angle for total internal reflection for incoupling into the light shaping unit. High-angle light may thus be provided to the skin.

In an embodiment, the light source includes one or more LEDs, the light shaping unit includes a transparent body having an inclined side portion and a flat center portion, and the one or more LEDs being arranged to provide light to the inclined side portion to couple light into the light shaping unit at angles larger than 55 degrees in the transparent body relative to the optical axis of the transparent body. The transparent body has an optical axis. The optical axis of the transparent body coincides with the optical axis of the dermoscope. For an exemplary transparent body made of glass with a refractive index of about 1.50 and water as an immersion fluid with a refractive index of about 1.34, light coupled into the light shaping unit at angles larger than 55 degrees in the transparent body relative to the optical axis of the transparent body, such as at angles in a range of 56-63 degrees, may be refracted at the transparent body-immersion fluid interface to be coupled in at angles larger than 70 degrees in the immersion fluid, such as at angles in a range of 72-76 degrees. The transparent body may e.g. be a frustoconically shaped body, or a right frustum, i.e. a clipped pyramid with a square base, or another polygonal frustrum, e.g. a n-polygon bottom surface with n trapezoidal side walls extending to a n-polygon top surface. The one or more LEDs thus provide light at angles into the transparent body that cannot be achieved in know systems where light is coupled in through air substantially in the direction of the optical axis through a flat cover glass. So, high-angle light may hereby be provided into the light shaping unit and from there to the skin. The inclined side portion may have an optically smooth surface for coupling light from the light source into the transparent body by pure refraction. Hereby, the width of the light beam projected into the glass is defined by, in particular, the beam angle of the light source, the spatial extension of the light source, the incident axis, the inclination angle and the refractive index of the transparent body. The inclined side portion may have a forward-scattering surface for coupling light from the light source into the transparent body by forward scattering. Hereby, the width of the light beam projected into the transparent body may be increased compared to an optically smooth surface, which may illuminate a larger part of the skin and thus provide a larger field-of-view. In a further embodiment, the flat center portion is arranged to direct at least part of the light refracted from the one or more at least partly transparent structures to the image forming lens to the image forming lens. In embodiments having the further light sources, the flat center portion is further arranged to direct the further light towards the part of the skin.

In an embodiment, the light source includes a plurality of selectively operable light source sections arranged to provide light to the light shaping unit in a plurality of directions for letting the light shaping unit direct the at least part of the light via the immersion fluid to the part of the skin having the one or more at least partly transparent structures to be imaged at incident angles in the immersion fluid larger than 70 degrees relative to the optical axis of the dermoscope at one or more of the plurality of directions. The selectively operable light source sections may e.g., be arranged in two sections, such as a left section and a right section. Operating the left section while not operating the right section allows to image all or most right edges of the transparent hair, while operating the right section while not operating the left section allows to image all or most left edges of the transparent hair. The selectively operable light source sections may alternatively be arranged in, e.g., four sections which could e.g. be referred to as an east, south, west and north section. A subset of the selectively operable light source sections may e.g. be used to get a reduced image complexity when there is a high density of structures in the image.

According to a second aspect, a sub-assembly for a dermoscope is provided. The sub-assembly includes a light source and a light shaping unit. The light source includes one or more LEDs. The light shaping unit includes a transparent body having an inclined side portion and a flat center portion. The one or more LEDs are arranged to provide light to the inclined side portion to couple light into the light shaping unit at angles larger than 55 degrees in the transparent body relative to the optical axis of the transparent body. The inclined side portion allows to couple light from air into the light shaping unit with angles relative to the optical axis inside the light shaping unit that would not be possible when a flat body would be used. The transparent body may e.g. be a frustoconically shaped body, or a topped pyramid. The one or more LEDs thus provide light at angles into the transparent body that cannot be achieved in know systems where light is coupled in through air substantially in the direction of the optical axis. So, high-angle light may hereby be provided into the light shaping unit and from there to the skin when the sub-assembly is used in a dermoscope. The transparent body may for example be made of, for example, glass, polycarbonate, or another optical plastic. The transparent body may have a refractive index in a range of 1.45-1.60, such as for example 1.50 for an exemplary type of glass. The light in the transparent body at angles larger than 55 degrees relative to the optical axis of the transparent body may thus be refracted into the immersion fluid at angles larger than 70 degrees in the immersion fluid and measure relative to the optical axis of the transparent body. In an exemplary embodiment, the transparent body is made of glass, the immersion fluid is water, and the one or more LEDs are arranged to provide light to the inclined side portion to couple light into the light shaping unit at angles in a range of 56-73 degrees in the transparent body relative to the optical axis of the transparent body. In a further embodiment, the flat center portion is arranged to direct at least part of the light refracted from the part of the skin to the image forming lens. In embodiments having the further light sources, the flat center portion may be further arranged to direct the further light towards the part of the skin.

A third aspect provides a system for assessment of hair and/or skin condition, the system including an dermoscope according to any one of the embodiments described above, an analysis unit arranged to receive one or more dermoscopy images from the dermoscope and to obtain a dermoscopic analysis result from the one or more dermoscopy images, the dermoscopic analysis result including at least one of an analysis result suitable for assessment of hair condition and an analysis result suitable for assessment of skin condition and a presentation unit arranged to receive the dermoscopic analysis result from the analysis unit and to present at least part of the analysis result to a user. Possible advantages of embodiments of the system according to the third aspect will be apparent from the advantages of the dermoscope of embodiments of the first aspect.

A fourth aspect provides a method for forming an image of a part of a skin. The method includes applying an immersion fluid on at least the part of the skin to be imaged, illuminating the at least the part of the skin having the one or more at least partly transparent structures to be imaged through the immersion fluid with light at incident angles relative to the normal to the part of the skin larger than 70 degrees, detecting at least part of the light refracted at return angles within a detection range from the one or more at least partly transparent structures of the part of the skin, and forming the image from at least the detected light. In an embodiment, the detection range may correspond to return angles smaller than a maximum detection angle. In a further embodiment, the maximum detection angle being in a range of 2-20 degrees relative to the normal to the part of the skin. In an example, the maximum detection angle is 20 degrees, such that the detection range may correspond to return angles smaller than 20 degrees relative to the normal of the skin surface. In another further embodiment, the maximum detection angle being in a range of 2-10 degrees relative to the normal to the part of the skin. In an example, the maximum detection angle is 10 degrees. In an example, the maximum detection angle is 5 degrees. Hereby, an image of hair and/or the skin, in particular the epidermis, may be obtained that also shows structures which would not have been visible, or poorly, in a known low-angle reflective method. The minimum incident angle and angular range are dependent on the immersion fluid used. In an embodiment, the immersion fluid is water or substantially water. For example, the immersion fluid can be water with a refractive index of approximately 1.34. With water, incident angles of 73 degrees or larger may be used for allowing to detect the refracted light. The immersion fluid can be alcohol with a refractive index of approximately 1.37. With alcohol, incident angles of 82 degrees or larger may be used for allowing to detect the refracted light. Further, with water, the distance between adjacent hairs needs to be approximately 2 to 3 hair diameters to be able to detect the hair reliable, as one hair may be in the shade of another hair if they are closer. For alcohol, the distance between adjacent hairs needs to be approximately 5 hair diameters. When the method is executed with a dermoscope according to one of the embodiments described above, the dermoscope may be used with the optical axis of the dermoscope corresponding to the normal of the skin surface, i.e., with the dermoscope arranged with the optical axis of the dermoscope perpendicular to the skin surface, for an optimal field-of-view.

In an embodiment, the method further includes illuminating the at least the part of the skin through the immersion fluid with further light at incident angles in the immersion fluid smaller than 48 degrees relative to the normal of the skin surface, the part of the skin further having one or more at least partly reflective structures, detecting at least part of the further light reflected from at least part of the one or more at least partly reflective structures, and forming the image or a further image from at least the detected further light. The further light may thus provide a reflective image of the part of the skin and structures thereon. The reflective image may in particular relate to dark hair and structure on the surface of the skin. In a further embodiment, the method includes selectively illuminating the at least the part of the skin at incident angles relative to the normal larger than 70 degrees and illuminating the at least the part of the skin at incident angles in the immersion fluid smaller than 48 degrees. In a further embodiment, the method includes switching between illuminating the at least the part of the skin at incident angles relative to the normal larger than 70 degrees and illuminating the at least the part of the skin at incident angles in the immersion fluid smaller than 48 degrees.

In an embodiment, illuminating the at least the part of the skin having the one or more at least partly transparent structures to be imaged through the immersion fluid at incident angles relative to the normal larger than 70 degrees is performed in at least two different angular ranges. For example, illumination may be done by illuminating the part of the skin from the right and from the left, allowing to independently detect the left and right sides—which may also referred to as edges—of hair. Discriminating between left and right side may e.g. be advantageous when the image is very busy and/or to revolve ambiguities.

A fifth aspect provides, a method for analyzing a skin and/or hair condition. The method includes obtaining an image registered by any one of the methods according to any of the embodiments described above, and detecting an edge of a transparent or semi-transparent hair in the image.

In an embodiment, the method includes detecting an opposite edge of the transparent or semi-transparent hair, and determining a diameter of the transparent or semi-transparent hair from the edge and the opposite edges of the hair transparent or semi-transparent hair. The method may provide a high accuracy of measuring the hair diameter.

In an embodiment, the method includes determining a position of each of at least two partially overlapping hair from using edges detected in the image corresponding to one of two opposite sides of each of the at least two partially overlapping hair. Hereby, a hair may be detected also when just a single edge is imaged with high-angle light.

A sixth aspect provides, a method for analyzing a skin and/or hair condition. The method includes obtaining an image using a dermoscope according to any of the embodiments described above and/or an image registered by any one of the methods according to any of the embodiments described above, and detecting a structure in an upper layer of the skin registered using at least part of the light provided the immersion fluid to the part of the skin having the one or more at least partly transparent structures to be imaged at incident angles in the immersion fluid larger than 70 degrees relative to the optical axis of the dermoscope and/or the normal of the skin surface. Structures in the upper layer of the skin, such as empty hair follicles, may hereby be imaged and further inspected and/or analyzed.

A seventh aspect provides a computer program product including a computer program including instructions arranged to, when executed by a computer, execute at least part of the method for analyzing a skin and/or hair condition according to any one embodiment.

BRIEF DESCRIPTION OF THE DRAWINGS

These and other aspects of the presently disclosed subject matter are apparent from and will be elucidated with reference to the embodiments described hereinafter. In the drawings, FIG. 1 schematically shows a system for assessment of hair and/or skin condition, FIG. 2 schematically shows a related art dermoscope, FIG. 3a schematically shows a dermoscope according to an embodiment, FIG. 3b schematically shows a part of a dermoscope according to an embodiment, FIG. 3c schematically shows a dermoscope according to another embodiment, FIG. 3d-FIG. 3d schematically shows parts of dermoscopes according to embodiments, FIG. 4a-FIG. 4d schematically show aspects of registering images with a dermoscope according to embodiments, FIG. 5 schematically shows a dermoscope according to another embodiment, FIG. 6 schematically shows a method for assessment of hair and/or skin condition according to embodiments.

It should be noted that items which have the same reference numbers in different Figures, have the same or corresponding structural features and the same or corresponding functions, or are the same or corresponding signals. Where the function and/or structure of such an item has been explained, there is no necessity for repeated explanation thereof in the detailed description.

DETAILED DESCRIPTION OF EXEMPLARY EMBODIMENTS

Figure 1:
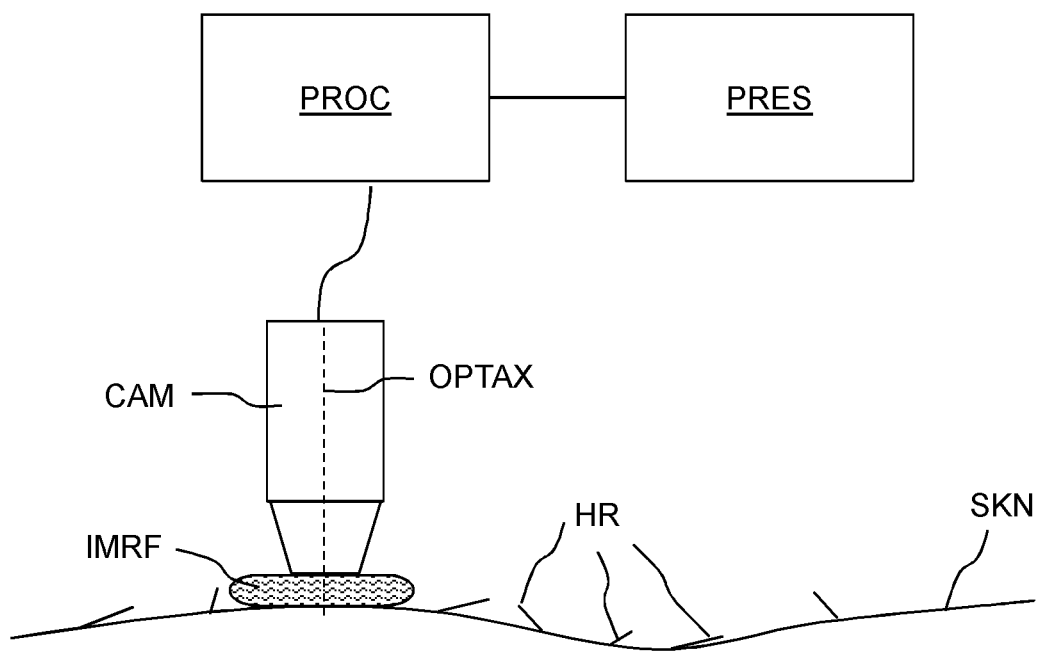

FIG. 1 schematically shows a system for assessment of hair and/or skin condition. The system shown in FIG. 1 has a dermoscope CAM, an analysis unit PROC and a presentation unit PRES. The dermoscope CAM is shown in use, where the dermascope is operate to form an image of a part of a skin SKN with some HR and to provide the image as a dermoscopy image to the analysis unit PRES. In imaging the part of the skin, an immersion fluid IMRF is used in between a cover glass (not shown) of the dermoscope CAM and the skin to reduce skin reflections. The analysis unit PRES is arranged to receive one or more dermoscopy images from the dermoscope CAM. The analysis unit PROC is arranged to obtain a dermoscopic analysis result from the one or more dermoscopy images. The dermoscopic analysis result may including at least one of an analysis result suitable for assessment of hair condition, such as a set of measurements of hair diameters or hair density, and an analysis result suitable for assessment of skin condition, such a count of empty hair follicle or an indicator of skin damage. The presentation unit PRES is arranged to receive the dermoscopic analysis result from the analysis unit PROC and to present at least part of the analysis result to a user. With a dermoscope CAM according to one or more embodiments described below, the dermoscope CAM may well image transparent hair. Further, in embodiments, the dermoscope CAM may image structures in the upper skin layer, such as emptry hair follicle and keratinized cells.

The system shown in FIG. 1 may thus be used in a method for forming an image of a part of a skin. The method may include applying an immersion fluid on at least the part of the skin to be imaged, illuminating the at least the part of the skin having the one or more at least partly transparent structures to be imaged through the immersion fluid, detecting at least part of the light received back from the part of the skin, and forming the image from at least the detected light.

Figure 2:
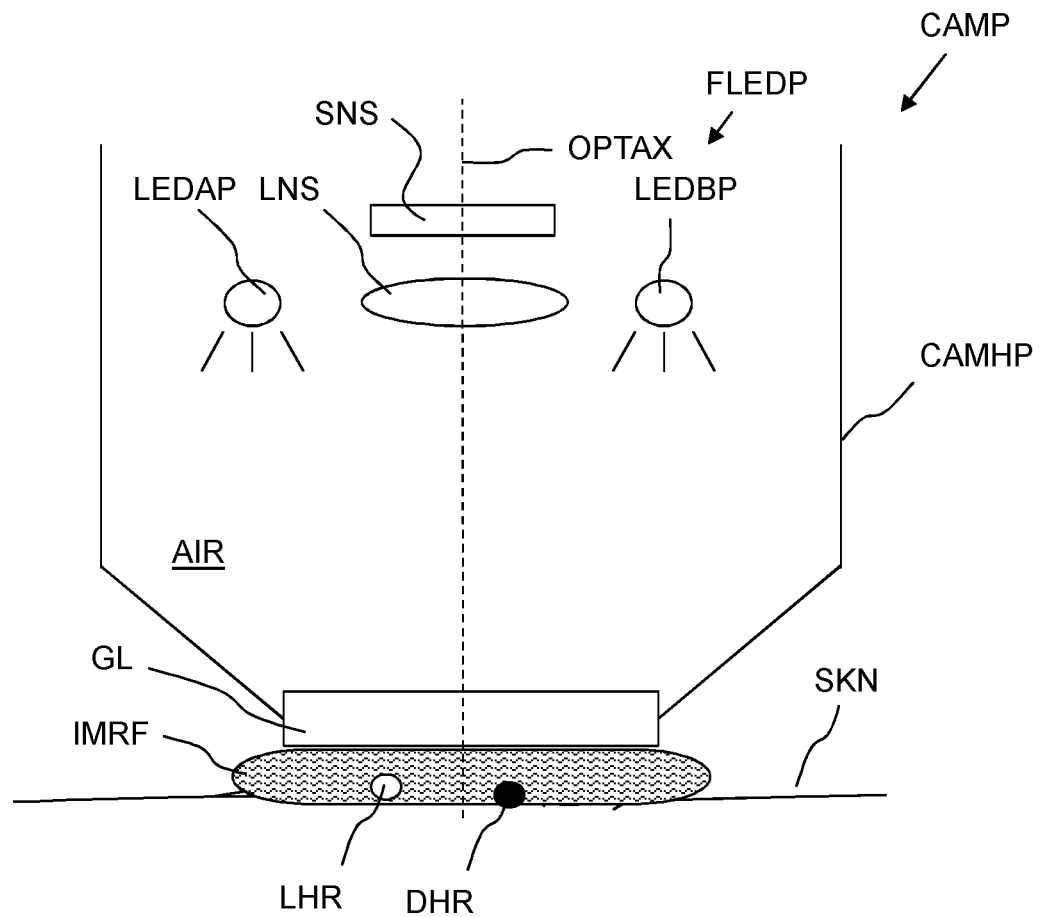

FIG. 2 schematically shows a known dermoscope CAMP. The known dermoscope CAMP has a light source FLEDP in the form of a plurality of LEDs LEDAP, LEDBP, an imaging lens LNS, a sensor SNS, and a cover glass GL in a dermoscope housing CAMHP. The imaging lens LNS and the sensor SNS are aligned on an optical axis OPTAX of the dermoscope. The cover glass GL is, at least substantially, perpendicular to the optical axis OPTAX. The plurality of LEDs LEDAP, LEDBP are arranged in a circular arrangement around the imaging lens LNS. The LEDs LEDAP, LEDBP are arranged in air at a distance from the cover glass GL and are arranged to provide light to the cover glass GL. For imaging, an immersion fluid IMRF is used between the cover glass GL and the skin SKN. A large fraction of the light incident on the cover glass will enter the cover glass, but some fraction will reflect sat the cover glass-immersion fluid interface at it will be beyond the critical angle. The major part of the light will refract into the immersion fluid, where it may reflect well on dark hair DHR, but where it will reflect poorly on transparent hair LHR. The reflected light will travel back to and largely through the cover glass GL, and to the image forming lens LNS. The image forming lens LNS is arranged to receive at least part of the light reflected from the part of the skin to the image forming lens. The image forming lens LNS is arranged to image the light onto the sensor SNS. The sensor is further arranged to register the image from at least the detected light. When transparent hair needs to be images with such known dermoscopes, a usual method involves dying the hair to obtain artificially dark-coloured hair.

Figure 3A:
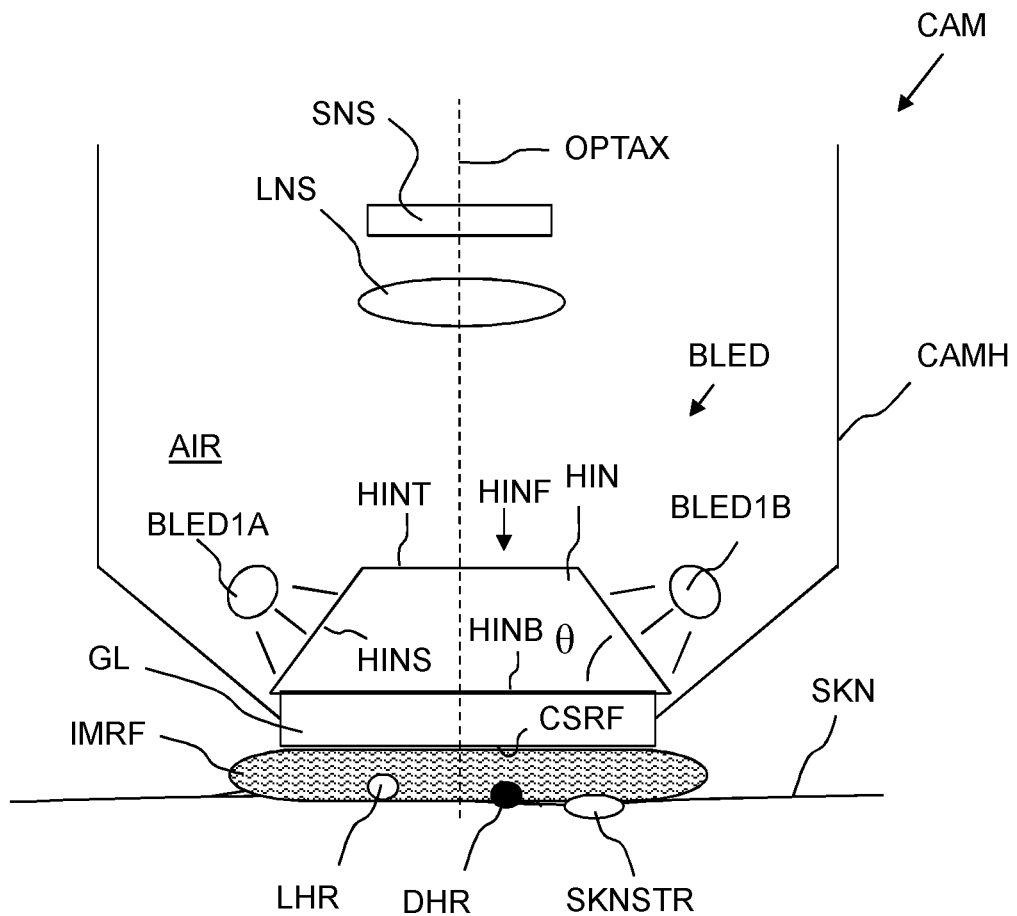

FIG. 3a schematically shows a dermoscope CAM for forming an image of a part of a skin having one or more at least partly transparent structures, such as at least party transparent hair, according to an embodiment. The dermoscope CAM has a light source BLED, a light shaping unit HIN, an image forming lens SNS, and, in the exemplary embodiment shown, a cover glass GL. The light shaping unit HIN and the imaging lens LNS are aligned on an optical axis OPTAX of the dermoscope. The cover glass GL is perpendicular to the optical axis OPTAX. The light shaping unit HIN is in optical contact with the cover glass GL. The shaping unit HIN may be made of the same material as the cover glass GL to effectively form an integrated body with substantially no reflective losses at the interface between them. The cover glass GL has an externally exposed contact surface CSRF. The contact surface CSRF is arranged to be in contact with an immersion fluid IMRF. In other embodiments, the cover glass GL and the light shaping unit HIN are formed as an integral unit, e.g., as schematically indicated in FIG. 3d and FIG. 3e. The light source BLED is drawn as two LEDs BLED1A, BLED1B, but it can include any suitable number of LEDs of one or of multiple types. The light source BLED is arranged to provide light to the light shaping unit HIN. The light shaping unit HIN is arranged to direct at least part of the light via the cover glass GL and via an immersion fluid IMRF to the part of the skin SKN to be imaged at incident angles (shown as a in FIG. 4a) in the immersion fluid larger than 70 degrees relative to the normal (shown as NOR in FIG. 4b) of the skin surface. The image forming lens LNS is arranged to receive at least part of the light refracted by the one or more at least partly transparent structures via the cover glass GL towards the image forming lens LNS. The dermoscope CAM shown in FIG. 3a further includes a sensor SNS. The sensor SNS and the image forming lens LNS are aligned on the optical axis OPTAX of the dermoscope. The image forming lens LNS is arranged to image the light onto the sensor SNS. The sensor SNS is further arranged to register the image from at least the detected light. The dermoscope CAM may alternatively include an eyepiece and the image forming lens may be part of the eyepiece or arranged to cooperate with the eyepiece. The dermoscope CAM allows for detecting and imaging transparent, grey or blond hair LHR using refraction and total internal reflection at the hairs inner surface, rather than reflection at it outer surface: the high-angle light is refracted into the transparent, grey or blond hair hair LHR, reflected by total internal reflection at the inner surface of the hair LHR, and refracted out of the hair LHR towards the imaging lens LNS and sensor SNS—or the eyepiece—, at lower angles, for example below 10° relative to the normal to the skin surface. Similarly may a structure SKNSTR in the upper layer of the skin SKN, such as structures with similar refractive index as hair and empty hair follicles, be detected and imaged using refraction of high-angle light and total internal reflection by such structure SKNSTR.

In the example shown in FIG. 3a, the light shaping unit HIN includes a transparent body having an inclined side portion HINS and a flat center portion HINF. The one or more LEDs BLED1A, BLED1B of the light source BLED are arranged to provide light to the inclined side portion HINS to couple light in to the light shaping unit at angles larger than 55 degrees relative to the optical axis of the transparent body. The flat center portion HINF has a flat top surface HINT and a flat bottom surface HINB, the bottom surface HINB being parallel to the top surface HINT. The top HINT and bottom surface HINB are perpendicular to the direction of the optical axis of the light shaping unit HIN. The top surface HINT is thus planparallel to the bottom surface HINB. The inclined side portion HINS extends from the bottom surface HINB to the top surface HINT at an inclination angle θ measured relative to the bottom surface HINB in a plane extending radially from the optical axis. The inclination angle θ may be 45 degrees, or any other suitable angle selected from a range of 30 to 90 degrees, in particular in a range of 30 to 60 degrees. The inclination angle θ may be designed in dependence on at least one parameter selected from the group of opening angle of the light beam from the LEDs BLED1A, BLED1B, refractive index of the transparent body of the light shaping unit HIN, refractive index of the immersion fluid IMRF, and wavelength range of the light from the LEDs BLED1A, BLED1B. In the example shown in FIG. 3a, the inclined side portion HINS has an optically smooth surface for coupling light from the light source BLED into the transparent body by pure refraction. In alternative examples, the inclined side portion may have a forward-scattering surface for coupling light from the light source into the transparent body by forward scattering, thereby, for example, illuminating a larger part of the skin than what would be obtained with pure refraction. The inclined side portion HINS allows to couple light from air into the light shaping unit with angles relative to the optical axis inside the light shaping unit that would not be possible when a flat, planparallel cover glass or a planparallel body would be used with light incident from its top surface, as can be understood from our description of FIG. 2 above.

With the refractive imaging with the dermoscope shown in FIG. 3a, refraction of light by hair can be used for detection and measurement of transparent hair. Further, measurements of hair pigmentation intensity inside of lightly pigmented hair may be performed. The dermoscope shown in FIG. 3a shown may be used in a method for forming an image of a part of a skin. The method may include applying an immersion fluid on at least the part of the skin to be imaged, illuminating the at least the part of the skin having the one or more at least partly transparent structures to be imaged through the immersion fluid at incident angles relative to the normal larger than 70 degrees in the immersion fluid, detecting at least part of the light received back from the part of the skin including light refracted from the part of the skin, and forming the image from at least the detected light.

Apart from imaging transparent hair, the same refractive imaging can also be used for detection of skin artefacts. For example, it has also been observed that outer layers of epidermis (stratum corneum) consist of material with similar refraction index as hair, so-called keratinized cells, and occurrences of their detachment can also be detected with the same optical setup. Also, the refractive imaging may be used to detect perifollicular scaling, and discriminate between normal and abnormal indicative of inflammation conditions. Detection of perifollicular scaling with no hair inside may be used to detect inactive follicles, complementary to yellow dots. Perifollicular scaling may for example be detected in refractive trichoscopy as it involves detached or loose keratinized cell structures around hair follicles. As empty follicles have similar structures, which may be used to detect hairless follicles, which may allow for a detection of advanced Androgenetic Alopecia (AGA).

As another example, comparison of refractive trichoscopic images of a fingerprint with sweat pore openings and the same finger after mechanical contact with a rough surface may show a resulting desquamation of outer corneum structures, and can be used to provide a qualitative as well as a quantitative measure of scaling around sweat pores as a result of intensive skin peeling.

Figure 3B:
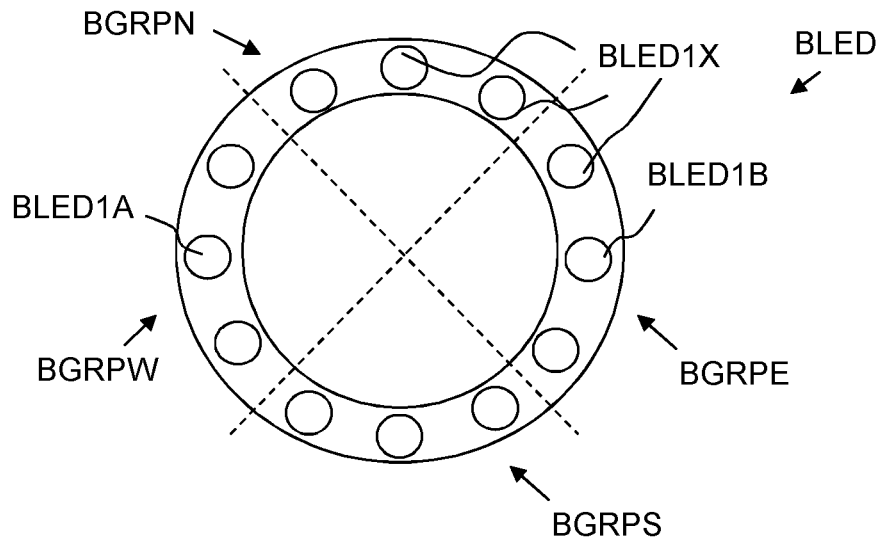

FIG. 3b schematically shows the light source BLED of the dermoscope CAM shown in FIG. 3a. The light source BLED includes a plurality of LEDs BKED1A, BLED1B, BLED1X arranged in a circular arrangement. FIG. 3b shows a plurality of 12 LEDs, but the number of LEDs may be any suitable number. The plurality of LEDs may be arranged in four groups, such as an 'East' group BGRPE, a 'South' group BGRPS, a 'West' group BGRPW and a 'North' group BGRPN, which may be independently operated. Operating the LEDs from the 'East' group may effectively result in an illumination at a high angle from the right ('East') side, whereby the left edges of transparent hair will be imaged (see below). A selective illumination with one or more segments may for example be of help in reliable detecting hair in images with overlapping hair. The light source BLED thus includes a plurality of selectively operable light source sections BGRPE, BGRPS, BGRPW, BGRPN arranged to provide light to the light shaping unit LIN in a plurality of directions for letting the light shaping unit direct the at least part of the light via the immersion fluid IMRF to the part of the skin having the one or more at least partly transparent structures to be imaged at incident angles in the immersion fluid larger than 70 degrees relative to the optical axis of the dermoscope at one or more of the plurality of directions.

A dermoscope having a light source shown in FIG. 3b shown may be used in a further method for forming an image of a part of a skin. The further method may include applying an immersion fluid on at least the part of the skin to be imaged, illuminating the at least the part of the skin having the one or more at least partly transparent structures to be imaged through the immersion fluid at incident angles relative to the normal larger than 70 degrees in the immersion fluid, detecting at least part of the light refracted from the one or more at least partly transparent structures, and forming the image from at least the detected light, wherein illuminating the at least the part of the skin having the one or more at least partly transparent structures to be imaged through the immersion fluid at incident angles relative to the normal larger than 70 degrees is performed in at least two different angular ranges. In the further method, illuminating the at least the part of the skin may include selectively directing at least part of the light via the immersion fluid to the part of the skin having the one or more at least partly transparent structures to be imaged at incident angles in the immersion fluid larger than 70 degrees relative to the optical axis of the dermoscope in one or more selected directions of a plurality of directions, the plurality of directions corresponding to the at least two different angular ranges. Selectively directing at least part of the light may be performed by selectively operating light source sections of a plurality of selectively operable light source sections BGRPE, BGRPS, BGRPW, BGRPN arranged to provide light to the light shaping unit LIN in a plurality of directions for letting the light shaping unit direct the at least part of the light via the immersion fluid IMRF to the part of the skin having the one or more at least partly transparent structures to be imaged at incident angles in the immersion fluid larger than 70 degrees relative to the optical axis of the dermoscope at one or more of the plurality of directions.

Figure 3C:
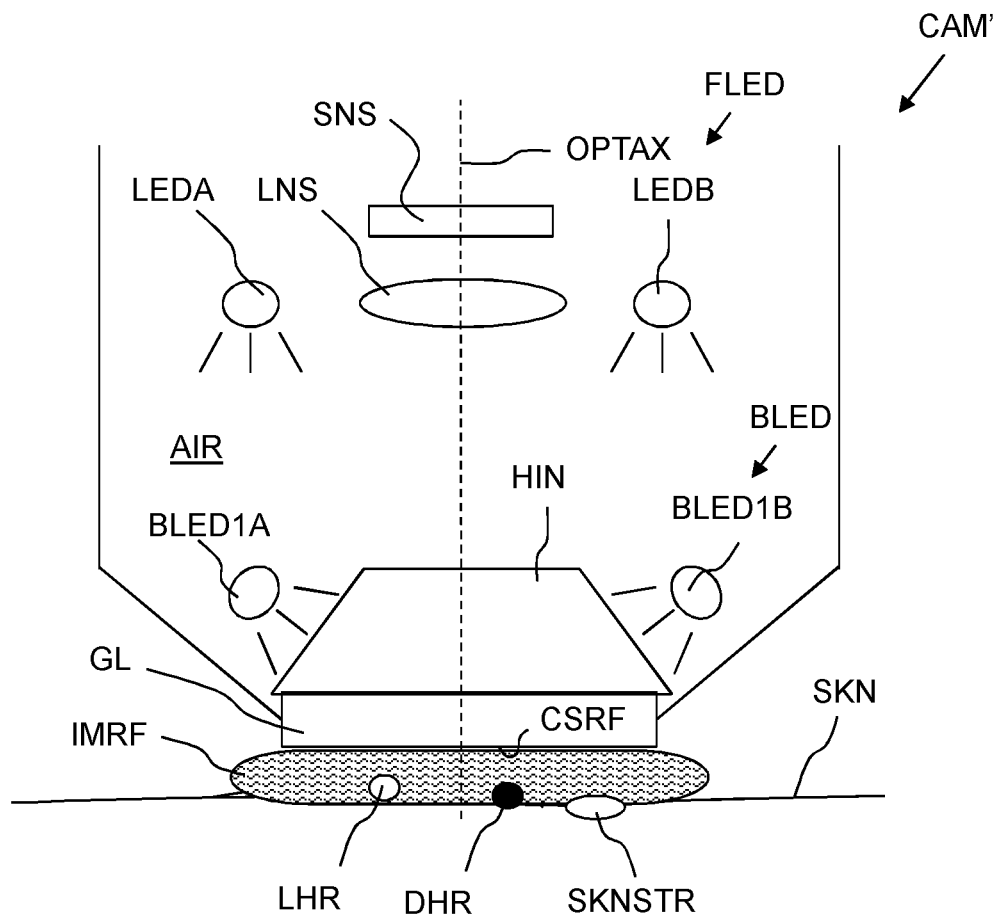
Figure 3D:
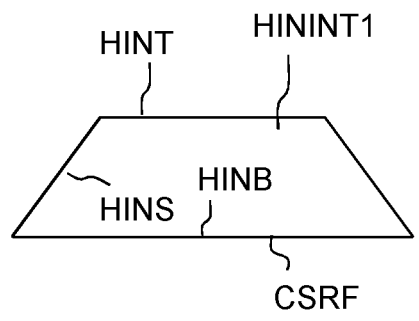
Figure 3E:
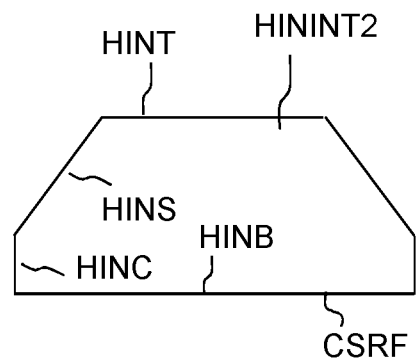

FIG. 3c schematically shows a dermoscope CAM' according to another embodiment. Reference is made to the description of FIG. 3a for corresponding features. The dermoscope CAM' is very similar to the dermoscope CAM shown in FIG. 3a, but differs from the dermoscope CAM in that the dermoscope CAM' also includes a further light source FLED. The further light source FLED is arranged to provide further light to the optical unit HIN for directing at least part of the further light at incident angles in the immersion fluid smaller than 48 degrees relative to the optical axis of the dermoscope. Light at this angle may be referred to as low-angle light. The low-angle light may be used for reflective imaging in a similar manner as in the related art dermoscope CAMP described with reference to FIG. 2. The further light source FLED may include a plurality of LEDs LEDA, LEDB. The plurality of LEDs LEDA, LEDB may be white LEDs. The further light source FLED may correspond to the light source used in the related art dermoscope shown in FIG. 2. In some embodiments, the dermoscope CAM is arranged to operate the light source BLED and the further light source FLED simulateneously. Herein, the dermoscope CAM may be arranged to operate the light source BLED and the further light source FLED at different brightnesses, for example to balance the brightness of the high-angle refractive and the low-angle reflective images. In some embodiments, the dermoscope CAM is arranged to selectively operate the light source BLED and the further light source FLED, such as sequentially or switching between the two.

FIG. 3d and FIG. 3e show examples of alternative light shaping units. The alternative light shaping units shown in FIG. 3d and FIG. 3e may be used to replace the light shaping unit HIN and the cover glass GL shown in FIG. 3a and FIG. 3c, and may be considered as light shaping units integrally formed with the cover glass. No separate contact glass GL may be necessary when such alternative light shaping unit is used. The same reference symbols as used in FIG. 3a and FIG. 3c are used where features of the alternative light shaping units substantially correspond to that of the light shaping unit HIN and the cover glass GL shown in FIG. 3a and FIG. 3c.

FIG. 3d shows an example of a light shaping unit HIN-INT1 including a transparent body having an inclined side portion HINS and a flat center portion HINF. The flat center portion HINF has a flat top surface HINT and a flat bottom surface HINB, the bottom surface HINB being parallel to the top surface HINT. The top HINT and bottom surface HINB are perpendicular to the direction of the optical axis of the light shaping unit HININT1. The inclined side portion HINS extends from the bottom surface HINB to the top surface HINT at an inclination angle. The inclined side portion HINS is designed to receive light from a light source and direct the light to the bottom surface HINB for high-angle illumination of the part of the skin, similar as in the embodiments shown in FIG. 3a and FIG. 3c. The bottom surface HINB is arranged to act as an external contact surface CSRF for contact with the immersion fluid on the part of the skin when using the dermoscope.

FIG. 3e shows another example of a light shaping unit HININT2 including a transparent body having a cylindrical side portion HINC, an inclined side portion HINS and a flat center portion HINF. The flat center portion HINF has a flat top surface HINT and a flat bottom surface HINB, the bottom surface HINB being parallel to the top surface HINT. The top HINT and bottom surface HINB are perpendicular to the direction of the optical axis of the light shaping unit HININT1. The cylindrical side portion HINC extends away from the bottom surface HINB to the inclined side portion HINS. The inclined side portion HINS extends from the cylindrical side portion HINC to the top surface HINT at an inclination angle. The inclined side portion HINS is designed to receive light from a light source and direct the light to the bottom surface HINB for high-angle illumination of the part of the skin. The bottom surface HINB is arranged to act as an external contact surface CSRF for contact with an immersion fluid on the part of the skin when using the dermoscope.

Figure 4A:
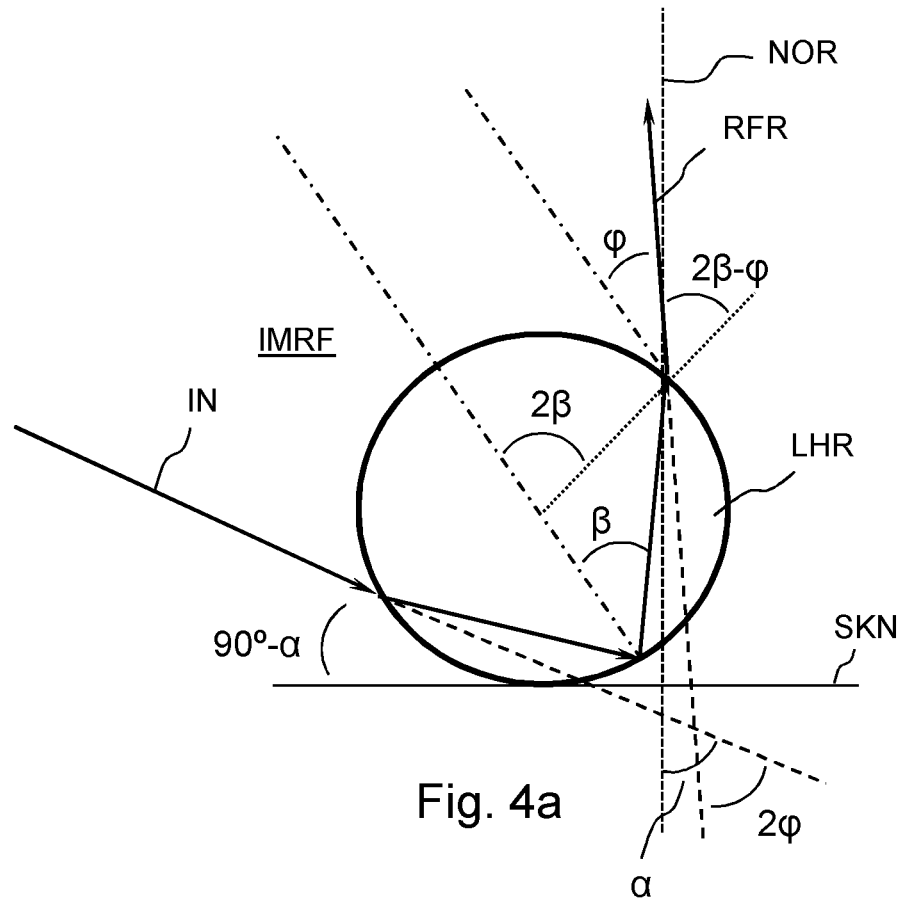

FIG. 4a schematically shows optics of refractive imaging. FIG. 4a shows a transparent hair LHR in an immersion fluid IMRF on a part of a skin SKN. An incident light ray IN impinges on the transparent hair LHR at an angle α relative to the normal NOR of the skin surface in the immersion fluid IMRF. The incident light ray IN is refracted by the immersion fluid-hair interface into the hair, then reflects by total internal reflection at the inside of the hair-immersion fluid interface, and is then refracted by the hair-immersion fluid interface to exit the hair as a refracted light lay RFR which proceeds via the cover glass GL and the light shaping unit HIN to the image forming lens SNS. The incident light ray IN is part of the high-angle light described before. With the refractive indices for the immersion fluid and the transparent hair indicated as n(fluid) and n(hair), Snell's refraction law gives:

$$n(\text{fluid})*\sin(2\beta-\varphi)=n(\text{hair})*\sin\beta$$

From this, it follows that a relation between incident and refracted ray direction reveals a maximum intensity at 2φ(max)—which may be further referred to as the first order rainbow angle—which depends on the refraction index ratio:

$$n(\text{rel})=n(\text{hair})/n(\text{fluid}).$$

The hair refraction index has been measured in humans to be 1.545 (male) and 1.550 (female). The hair immersed in alcohol (n=1.36) displays a relative refractive index n(rel) =1.14, while the same hair immersed in water (n=1.33) displays a relative refractive index n(rel)=1.16. The expected first order rainbow angle for hair is 80-82° or alcohol immersion and 73-75° for water immersion. To get 73-93° in water/alcohol, you need to project at 57-62° in glass (n=1.50). As these angles are much beyond the total internal reflection angle (49° and 47° for water and alcohol respectively), it is not possible to get that light there from a related art dermoscope having air between LED and flat contact glass as illustrated in FIG. 2). In an embodiment, a higher n substance is provided between the LED and the contact glass. In another embodiment, the LEDs are directly attached to the contact glass and/or an intermediate light shaping unit. Herein, directly attached means that no air is in between the LED and the contact glass, such that high-angle rays are not blocked by the critical angle of total internal reflection at one or more interfaces. In a further embodiment, the LEDs are directly attached to the contact glass and/or an intermediate light shaping unit and the incidence angle of light inside glass relative to camera is in a range of 57-62° relative to the optical axis.

The intensity of the refracted light may be used a measure of hair pigmentation intensity.

The (first order) refraction angle may provide for a measurement of a refraction index of a hair relative to the immersion fluid, and may be used to conclude on physical properties of the substance the hair is made of, like the density or water content.

Figure 4B:
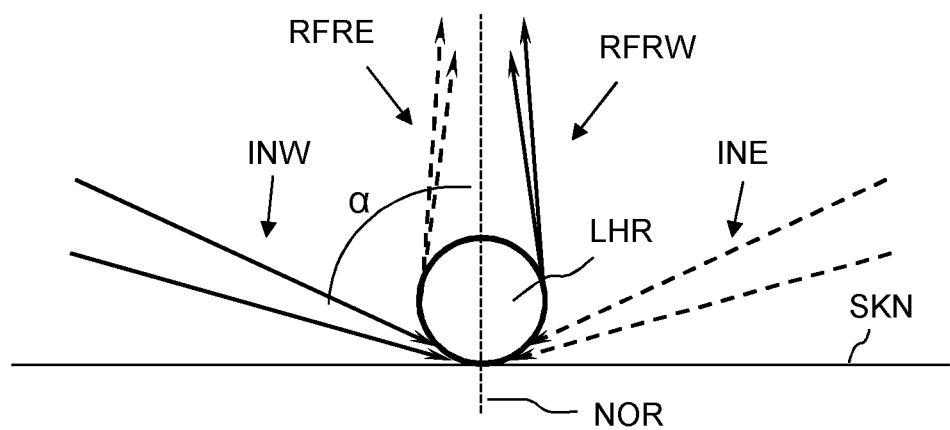

FIG. 4b schematically shows illumination from two sides. FIG. 4b shows a light hair LHR on a part of a skin SKN. Incident rays INW at angle of incidence a from the left-side of the figure impinge on the light hair LHR from the left and result in refracted rays RFRW proceeding in the direction of the image forming lens from the right edge of the light hair LHR. The incident rays INW may e.g, be provided by the 'East' group BGRPE of the plurality of LEDs of the light source shown in FIG. 3b. Incident rays INE α from the right-side of the figure impinge on the light hair LHR from the right and result in refracted rays RFRE proceeding in the direction of the image forming lens from the left edge of the light hair LHR. The incident rays INE may e.g, be provided by the 'West' group BGRPW of the plurality of LEDs of the light source shown in FIG. 3b.

Figure 4C:
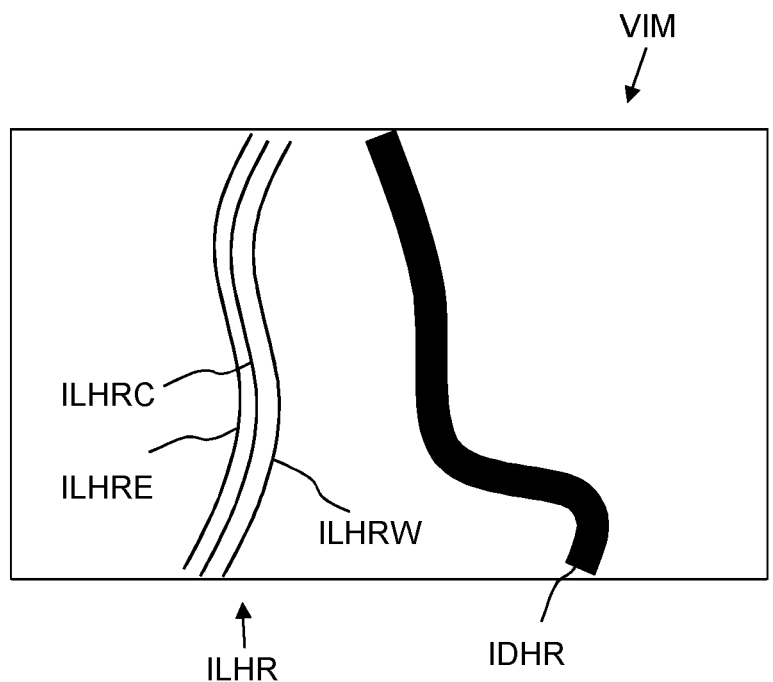

FIG. 4c schematically shows a dermoscopy image VIM registered with a dermoscope according to embodiments. The dermoscopy image VIM shows an image of a dark hair IDHR and an image of a transparent hair ILHR. The image of the dark hair IDHR is a reflective image, obtained from direct reflection at the outer hair surface. The image of the transparent hair ILHR is a refractive image and includes a refractive image ILHRE of the left edge obtained from high-angle light incident from the right (referring to the directions from FIG. 4b), a refractive image ILHRW of the right edge obtained from high-angle light incident from the left and, at a lesser intensity, a reflective image ILHRC, obtained from light incident at low angles. The refractive image and the reflective image may have been obtained from a simultaneously illumination with high-angle and low-angle light and together form the dermoscopy image VIM. The refractive image and the reflective image may alternatively have been obtained sequentially from a sequential illumination with high-angle and low-angle light and then combined into the dermoscopy image VIM.

In embodiments, the diameter of a transparent hair is determined from detecting both edges of the transparent hair.

Figure 4D:
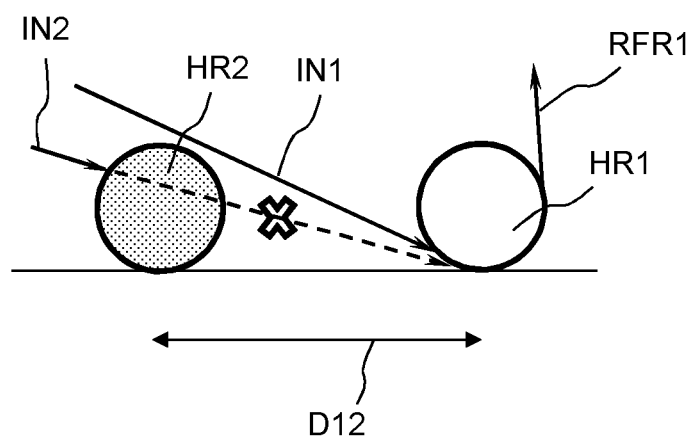

FIG. 4d schematically show aspects obtaining an image with a dermoscope according to embodiments when two hair are closely together. FIG. 4d shows a first, transparent hair, HR1 and a second, grey or black, hair HR2 at a distance D12 from the first hair HR1. A first incident ray IN1 impinges on the transparent hair HR1 where it is refracted into a refracted ray RFR1. However, a second incident ray IN2 is blocked by the second hair. As a result, the right edge of HR1 may be imaged, but the image does not show the left side. The blocking may occur if the hair are closer than about 3.5 diameters when alcohol is used as an immersion fluid; or if the hair are closer than about 7 diameters when water is used as an immersion fluid. The user may, if such effect is visible in the image, wish to rearrange the hair, e.g. by combing, and then obtain a new image.

In embodiments, the immersion fluid is water. As water as a lower refraction index than alcohol, less blocking of very-high-angle light may occur. Water as immersion fluid may thus allow a more complete image, and/or a better diameter measurement on transparent hair.

Figure 5:
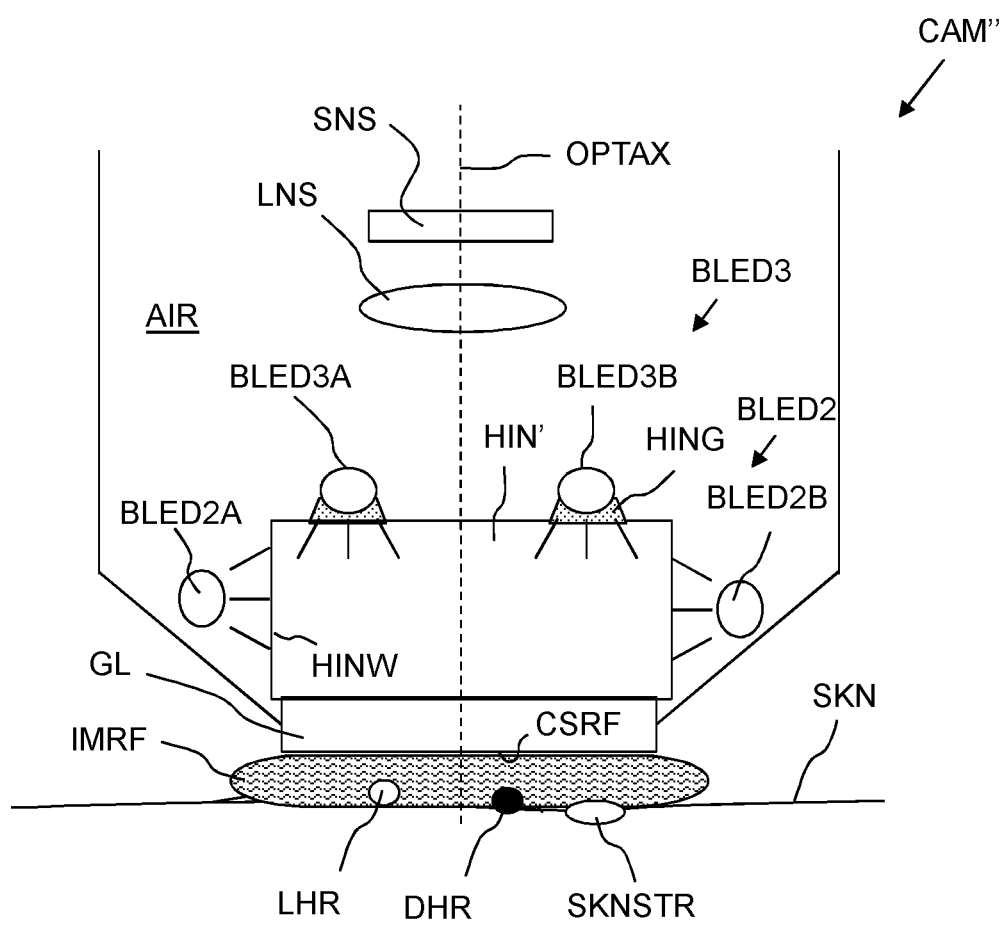

FIG. 5 schematically shows another dermoscope CAM" for forming an image of a part of a skin having one or more at least partly transparent structures, such as at least party transparent hair, according to an embodiment. Reference is made to the description of FIG. 3a for corresponding features. The dermoscope CAM" is very similar to the dermoscope CAM shown in FIG. 3a, but differs in that light shaping unit HIN is replaced by light shaping unit HIN'. Further, light source BLED is replaced by a side light source BLED2 including a plurality of side LEDs BLED2A, BLED2B and an attached light source BLED3 including a plurality of attached LEDs BLED3A, BLED3B. The light shaping unit HIN' may be a glass disk or rod, or a plastic disk or rod, or any other suitable optically transparent material. The light shaping unit HIN' may have a flat top surface and a flat bottom surface, the bottom surface being parallel to the bottom surface, measured in a direction of its optical axis. The top surface is thus planparallel to the bottom surface.

The light shaping unit HIN' may have a cylindrical wall HINW extending from the bottom surface to the top surface. The side light source BLED2 including a plurality of side LEDs BLED2A, BLED2B may be arranged to provide light to the cylindrical wall to couple light into the light shaping unit HIN' from the side at high angles relative to the optical axis of the light shaping unit HIN'. The attached light source BLED3 including the plurality of attached LEDs BLED3A, BLED3B is attached to the top surface of the light shaping unit HIN' with the attached LEDs BLED3A, BLED3B in direct optical contact with the light shaping unit. Hereto, the attached LEDs BLED3A, BLED3B may have been glued with an optically transparent glue HING to the light shaping unit HIN', whereby an optical connection is created without any air layer in between the attached LEDs and the light shaping unit HIN'. The light source BLED3 may thus include one or more LEDs BLED3A, BLED3B, with the one or more LEDs being in direct optical contact to the light shaping unit LIN', the one or more LEDs BLED3A, BLED3B thereby being arranged to couple light into the light shaping unit LIN' at angles larger than 55 degrees relative to the optical axis of the light shaping unit. Light at angles larger than 55 degrees in the material of the light shaping unit and relative to the optical axis of the light shaping unit, for example glass or plastic, may be projected at angles larger than 70 degrees in the immersion fluid relative to the surface of the skin. The skilled person will appreciate that the embodiments shown in FIG. 5 and FIG. 3a may be combined to form a further embodiment where attached LEDs BLED3A, BLED3B are attached to the top surface of a light shaping unit with an inclined side portion similar to the light shaping unit HIN shown in FIG. 3, and where one or more LEDs BLED1A, BLED1B of the light source BLED shown in FIG. 3 are arranged to provide light to the inclined side portion HINS. The skilled person will appreciate that the cover glass GL and the light shaping unit HIN' may be formed as an integral body, similar to the alternative light shaping unit HININT1 and HININT2 shown in FIG. 3d and FIG. 3e.

Figure 6:
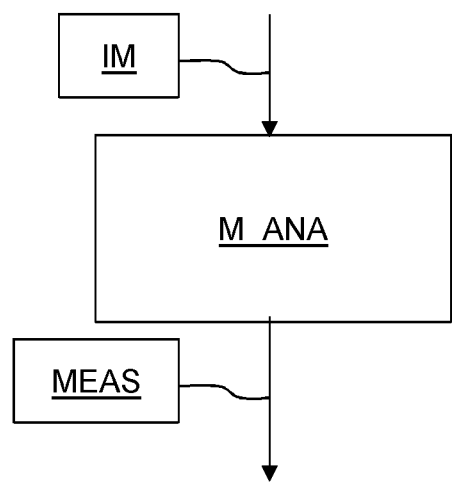

FIG. 6 shows a method for analyzing a skin and/or hair condition. The method may be executed the analysis unit PROC of the system shown in FIG. 1. The method includes obtaining an image IM formed using refractive trichoscopy as described above, i.e. from applying an immersion fluid on at least the part of the skin to be imaged, illuminating the at least the part of the skin having the one or more at least partly transparent structures to be imaged through the immersion fluid at incident angles relative to the normal larger than 70 degrees in the immersion fluid, detecting at least part of the light refracted from the one or more at least partly transparent structures of the part of the skin, and forming the image from at least the detected light. The image IM may be obtained directly from a dersmoscope CAM, as shown in FIG. 1, or retrieved from a storage unit (now shown). The method includes analyzing M_ANA the image IM to generate an analysis result MEAS, which may, e.g., be provided to the presentation unit PRES shown in FIG. 1, used for further analysis, or stored for later retrieval.

In an embodiment, analyzing M_ANA the image IM includes detecting an edge of a transparent or semi-transparent hair in the image, such as a blond or grey hair. An edge of a hair relates to an image of a part of a wall of a hair and may relate to a refractive image for a transparent hair. The detected edge or plurality of detected edges may be provided as part of the analysis result MEAS and/or used in further analysis.

The analyzing M_ANA may further include detecting an opposite edge of the transparent or semi-transparent hair, and determining a diameter of the transparent or semi-transparent hair from the edge and the opposite edges of the hair transparent or semi-transparent hair. Reference is made to the description of FIG. 4c above. The determined diameter(s) may be provided as part of the analysis result MEAS and/or used in further analysis.

The analyzing M_ANA may additionally or alternatively include determining a position of each of at least two partially overlapping hair from edges detected in the image corresponding to one of two opposite sides of each of the at least two partially overlapping hair. Reference is made to the description of FIG. 4d above.

Figure 7:
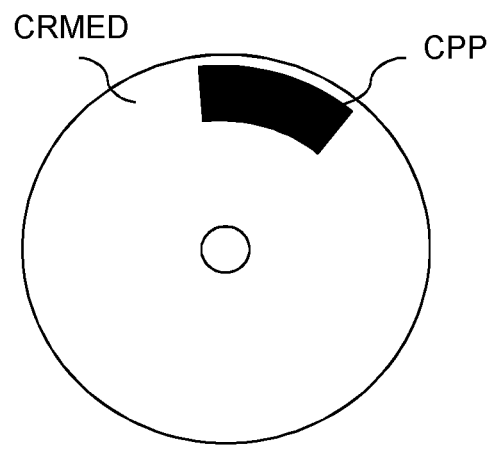
FIG. 7 shows a computer readable medium including a computer program product.

FIG. 7 shows a computer readable medium CRMED including a computer program product CPP, the computer program product CPP including instructions for causing a processor apparatus to perform a method according to any one embodiment or a part of thereof. The computer program product CPP may be embodied on the computer readable medium CRMED as physical marks or by magnetization of the computer readable medium CPP. However, any other suitable embodiment is conceivable as well. Furthermore, it will be appreciated that, although the computer readable medium CRMED is shown in FIG. 7 as an optical disc, the computer readable medium CRMED may be any suitable computer readable medium, such as a hard disk, solid state memory, flash memory, etc., and may be non-recordable or recordable. The computer program product CPP may thus include a computer program including instructions arranged to, when executed by a computer, execute at least part of the method of any one of the embodiments described above.

It should be noted that the above-mentioned embodiments illustrate rather than limit the presently disclosed subject matter, and that those skilled in the art will be able to design many alternative embodiments.

The presently disclosed subject matter may also be implemented in a computer program for running on a computer system, at least including code portions for performing steps of a method according to the presently disclosed subject matter when run on a programmable apparatus, such as a computer system or enabling a programmable apparatus to perform functions of a device or system according to the presently disclosed subject matter. The computer program may for instance include one or more of: a subroutine, a function, a procedure, an object method, an object implementation, an executable application, an applet, a servlet, a source code, an object code, a shared library/dynamic load library and/or other sequence of instructions designed for execution on a computer system. The computer program may be provided on a data carrier, such as a CD-type optical disc, a DVD-type optical disc, a hard disk, or diskette, stored with data loadable in a memory of a computer system, the data representing the computer program. The data carrier may thus be a tangible data carrier. The data carrier may be a data connection, such as a telephone cable or a network cable. The data carrier may further be a non-tangible data carrier such as a wireless connection.

In the claims, any reference signs placed between parentheses shall not be construed as limiting the claim. Use of the verb "include" and its conjugations does not exclude the presence of elements or steps other than those stated in a claim. The article "a" or "an" preceding an element does not exclude the presence of a plurality of such elements. The presently disclosed subject matter may be implemented by hardware including several distinct elements, and by a suitably programmed computer. In the device claim enumerating several elements, these elements may be embodied by one and the same item of hardware. The mere fact that certain measures are recited in mutually different dependent claims does not indicate that a combination of these measures cannot be used to advantage.

The invention claimed is:

1. A dermoscope for forming an image of a part of a skin having one or more at least partly transparent structures, the dermoscope comprising:
    a light source;
    a light shaping unit; and
    an image forming lens,
    wherein the light source, the light shaping unit and the image forming lens are aligned with an optical axis of the dermoscope,
    wherein the light source is configured to provide light to the light shaping unit,
    wherein the light shaping unit is configured to direct at least part of the light via an immersion fluid to the part of the skin having the one or more at least partly transparent structures to be imaged at incident angles in the immersion fluid larger than 70 degrees relative to the optical axis of the dermoscope,
    wherein the image forming lens is configured to receive at least part of the light refracted by the one or more at least partly transparent structures, and
    wherein the immersion fluid has a refractive index in a range of 1.33 to 1.37.

2. The dermoscope according to claim 1, further comprising a sensor configured to receive the light from the image forming lens and to register the image from at least the received light.

3. The dermoscope according to claim 1, further comprising a further light source configured to provide further light to the light shaping unit for directing at least part of the further light via the immersion fluid to the part of the skin to be imaged at incident angles in the immersion fluid smaller than 48 degrees relative to the optical axis of the dermoscope,
    wherein the image forming lens is configured to receive at least part of the further light reflected from the part of the skin, the part of the skin further having one or more at least partly reflective structures.

4. The dermoscope according to claim 3, wherein the dermoscope is configured to selectively operate the light source and the further light source.

5. The dermoscope according to claim 1, wherein
    the light source includes one or more Light Emitting Diodes (LEDs), and
    the one or more LEDs are in direct optical contact to the light shaping unit, the one or more LEDs thereby being configured to couple light into the light shaping unit at angles larger than 55 degrees relative to the optical axis of the dermoscope.

6. The dermoscope according to claim 1, wherein
    the light source includes one or more Light Emitting Diodes (LEDs),
    wherein the light shaping unit includes a transparent body having an inclined side portion and a flat center portion, the transparent body having an optical axis, the optical axis of the transparent body coinciding with the optical axis of the dermoscope,
    wherein the one or more LEDs are configured to provide light to the inclined side portion to couple light into the light shaping unit at angles in the transparent body larger than 55 degrees relative to the optical axis of the transparent body, and
    wherein the flat center portion is configured to direct at least part of the light refracted from the one or more at least partly transparent structures to the image forming lens.

7. The dermoscope according to claim 1, wherein the light source includes a plurality of selectively operable light source sections arranged to provide light to the light shaping unit in a plurality of directions for letting the light shaping unit direct the at least part of the light via the immersion fluid to the part of the skin having the one or more at least partly transparent structures to be imaged at incident angles in the immersion fluid larger than 70 degrees relative to the optical axis of the dermoscope at one or more of the plurality of directions.

8. A system for assessment of a hair and/or skin condition, the system comprising:
    a dermoscope;
    an analysis unit; and
    a presentation unit,
    wherein the dermoscope is a dermoscope for forming an image of a part of a skin having one or more at least partly transparent structures, the dermoscope comprising:
    a light source;
    a light shaping unit; and
    an image forming lens,
    wherein the light source, the light shaping unit and the image forming lens are aligned with an optical axis of the dermoscope,
    wherein the light source is configured to provide light to the light shaping unit,
    wherein the light shaping unit is configured to direct at least part of the light via an immersion fluid to the part of the skin having the one or more at least partly transparent structures to be imaged at incident angles in the immersion fluid larger than 70 degrees relative to the optical axis of the dermoscope,
    wherein the image forming lens is configured to receive at least part of the light refracted by the one or more at least partly transparent structures, and
    wherein the immersion fluid has a refractive index in a range of 1.33 to 1.37;
    and
    wherein the analysis unit is configured to receive one or more dermoscopy images from the dermoscope and to obtain a dermoscopic analysis result from the one or more dermoscopy images, the dermoscopic analysis result including at least one of:
    an analysis result suitable for assessment of hair condition, and
    an analysis result suitable for assessment of skin condition, and
    the presentation unit is configured to receive the dermoscopic analysis result from the analysis unit and to present at least part of the analysis result to a user.

9. A method for forming an image of a part of a skin having one or more at least partly transparent structures, the method comprising:
    applying an immersion fluid on at least the part of the skin having the one or more at least partly transparent structures to be imaged, and the immersion fluid has a refractive index in a range of 1.33 to 1.37;
    illuminating the at least the part of the skin having the one or more at least partly transparent structures to be imaged through the immersion fluid at incident angles relative to a normal to the part of the skin larger than 70 degrees in the immersion fluid;

detecting at least part of light refracted at return angles within a detection range from the one or more at least partly transparent structures to obtain detected light; and forming the image from at least the detected light.

10. The method according to claim 9 further comprising:

illuminating the at least the part of the skin through the immersion fluid with further at incident angles in the immersion fluid smaller than 48 degrees relative to the normal of the part of the skin surface;

detecting at least part of a further light reflected at a return angles within the detection range from reflective structures of the part of the skin to obtain detected further light; and forming the image or forming a further image from at least the detected further light.

11. The method according to claim 9, wherein illuminating the at least the part of the skin having the one or more at least partly transparent structures to be imaged through the immersion fluid at incident angles relative to the normal larger than 70 degrees is performed in at least two different angular ranges.

12. The method of claim 9 further comprising:

analyzing a skin and/or hair condition by obtaining the image and detecting an edge of a transparent or semi-transparent hair in the image.

13. The method according to claim 12 further comprising:

detecting an opposite edge of the transparent or semi-transparent hair; and determining a diameter of the transparent or semi-transparent hair from the edge and the opposite edge of the transparent or semi-transparent hair.

14. The method according to claim 12 further comprising:

determining a position of each of at least two partially overlapping hair from using edges detected in the image corresponding to one of two opposite sides of each of the at least two partially overlapping hairs.

15. The method according to claim 12 further comprising:

a non-transitory computer-readable storage medium storing instructions that when executed by a computer cause the computer to perform the method.

* * * * *